United States Patent [19]

Thakkar

[11] 3,988,439
[45] Oct. 26, 1976

[54] DIBENZO[b,d]PYRANONE DISPERSIONS

[75] Inventor: Arvind L. Thakkar, Indianapolis, Ind.

[73] Assignee: Eli Lilly and Company, Indianapolis, Ind.

[22] Filed: June 23, 1975

[21] Appl. No.: 589,311

Related U.S. Application Data

[62] Division of Ser. No. 413,012, Nov. 5, 1973, Pat. No. 3,920,809.

[52] U.S. Cl.................................. 424/78; 424/283
[51] Int. Cl.² ........................................ A61K 31/74
[58] Field of Search ............................. 424/283, 78

[56] References Cited

UNITED STATES PATENTS

| 3,507,885 | 4/1970 | Fahrenholtz | 260/345.3 |
| 3,636,058 | 1/1972 | Fahrenholtz | 260/345.34 |

*Primary Examiner*—Jerome D. Goldberg
*Attorney, Agent, or Firm*—James L. Rowe; Everet F. Smith

[57] ABSTRACT

1-Hydroxy-3-alkyl-9-keto or 9-hydroxyhexahydro dibenzo[b,d]pyrans, useful as tranquilizers or hypotensive agents are dispersed with PVP or polyethylene glycol.

2 Claims, No Drawings

DIBENZO[b,d]PYRANONE DISPERSIONS

This is a division of application Ser. No. 413,012 filed Nov. 5, 1973, now U.S. Pat. No. 3,920,809.

BACKGROUND OF THE INVENTION

1-Hydroxy-3-alkyl-6,6a,7,8,10,10a-hexahydro-9H-dibenzo [b,d]pyran-9-ones, their ethers and esters are disclosed in U.S. Pat. No. 3,507,885 as intermediates for the preparation of $\Delta^8$ or $\Delta^9$-tetrahydrocannabinols ($\Delta^8$ or $\Delta^9$-THC). No other utility than as intermediates is disclosed for these compounds.

Polyvinylpyrrolidone (PVP) has been used to increase the solubility of aromatic compounds. Among these aromatic compounds have been several useful drugs. In particular, PVP complexing has been employed to increase the solubility of the drug for intravenous injection. The following papers deal with the use of PVP in injectable preparations containing $\Delta^9$-THC: D. C. Fennimore and P. R. Loy, *J. Pharm. Pharmac.* 23, 310 (1971) and H. Rosenkrantz et al., *J. Pharm. Sci.*, 61, 1106 (1972). Publication detailing the use of PVP complexes with other drugs include the following: E. I. Stupak and T. R. Bates, *J. Pharm. Sci.*, 61, 400 (1972) W. L. Chiou and S. Riegelman, ibid, 60. 1281 (1971), 58, 1505 (1969), 59, 937 (1970), G. R. Svoboda, M. J. Sweeney and W. D. Walking, ibid, 60, 33 (1971), P. Molyneux and H. Frank, *J. Am. Chem. Soc.*, 83, 3169 (1961), T. hiquchi et al., *J. Am. Pharm. Assoc., Sci. Ed.*, 43, 393 (1954), ibid, 398 (1954). M. Mayersohn et al., *J. Pharm. Sci.*, 55, 1323 (1966), A. P. Simonelli et al., *J. Pharm. Sci.* 58, 538 (1969), and J. P. Davignon, *Bull. Parent Drug Assoc.*, 23, 83 (1969).

U.S. Pat. No. 3,673,163 discloses and claims a coprecipitate of the tricyclic compound, acronycine, with polyvinylpyrrolidone, said co-precipitate providing an acronycine dosage form of increased solubility.

$\Delta^9$-THC and other structurally related derivatives, either obtainable from natural sources or from various synthetic procedures, are known to be extremely insoluble in aqueous media. Consequently, there has been a continuing problem in determining the pharmacological activities of this group of compounds when administered by the oral route since there has been uncertainty as to the degree of absorption of these extremely insoluble substances after oral administration. Dispersions of dibenzo[b,d]pyran-9-ones with PVP or other similar materials for oral administration have not hitherto been described.

SUMMARY OF THE INVENTION

This invention provides dispersions of a compound represented by the formula

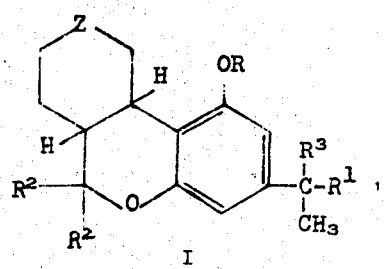

wherein Z is

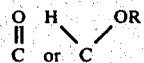

wherein each R is individually hydrogen or $C_1$-$C_3$ alkanoyl, wherein each $R^2$ is either hydrogen or methyl, and both $R^2$ groups are the same, wherein $R^3$ is hydrogen or methyl, and wherein $R^1$ is $C_1$-$C_6$ alkyl or $C_2$-$C_6$ alkenyl
with a polyvinylpyrrolidone (PVP) having a molecular weight in the range of 10,000–360,000 or a polyethylene glycol having a molecular weight in the range 1000–6000.

In the above formula the term "$C_1$-$C_3$ alkanoyl" includes the groups: acetyl, propionyl, butyryl and isobutyryl. The scope of the grouping

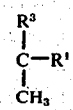

is illustrated by the following radicals:
1,2-dimethylheptyl, 1,1-dimethylheptyl, 1,2-dimethylhexyl, 1,1-dimethylpentyl, 1,1-dimethylpropyl, 1-methylbutyl, 1-methyloctyl, 1-methylheptyl, 1-methylhexyl, 1,2-dimethyl-3-hexenyl, 1,1-dimethyl-2-heptenyl, 1-methyl-2-butenyl. The following tetrahydrodibenzopyrans are among compounds useful in the compositions of this invention:

1-hydroxy-3-n-heptyl-6,6a,7,8,10,10a-hexahydro-9H-dibenzo[b,d] pyran-9-one, 1-hydroxy-3-n-nonyl-6,6-dimethyl-6,6a,7,8,10,10a-hexahydro-9H-dibenzo[b,d]pyran-9-one 1-hydroxy-3-(1'-methyl-2'-butenyl)-6,6-dimethyl-6,6a,7,8,10,10a,-hexahydro-9H-dibenzo[b,d]pyran-9-one.

1-propionoxy-3-(1'-methylheptyl)-6,6-dimethyl-6,6a,7,8,10,10a-hexahydro-9H-dibenzo[b,d]pyran-9-one, 1,9-dihydroxy-3-(1'-methylheptyl)-6,6-dimethyl-6a,7,8,9,10,10a-hexahydro-6H-dibenzo[b,d]pyran, 1,9-dihydroxy-3-(1',1'-dimethylheptyl)-6,6-dimethyl-6a,7,8,9,10,10a,-hexahydro-6H-dibenzo[b,d]pyran, 1-butyroxy-3-(1',2'-dimethylheptyl)-6,6-dimethyl-6,6a,7,8,10,10a-hexahydro-9H-dibenzo[b,d]pyran-9-one 1,9-dihydroxy-3-(1',1'-dimethyl-2'-butenyl)-6a,7,8,9,10,10a,-hexahydro-6H-dibenzo[b,d]pyran.

The dispersions of this invention contain from one part of a compound represented by the above formula to 2–20 parts of a PVP of molecular weight 10,000–360,000 or of a polyethylene glycol of molecular weight 1000–6000. The dispersions are prepared by dissolving the drug and the dispersing agent separately, preferably in a mutual solvent such as ethanol, mixing the two solutions and evaporating the solvent or solvents. Dispersions prepared in this fashion are useful in the preparation of pharmaceutical formulations of the above compounds for administration to mammals. For example, a complex containing one part of 1-hydroxy-3-(1',1'-dimethylheptyl)-6,6-dimethyl-6,6a,7,8,10,-10a-hexahydro-9H-dibenzo[b,d]pyran-9-one and nine parts of PVP (molecular weight = 40,000) is mixed with an appropriate amount of a suitable excipient, for example, starch, and the mixture placed in telescoping gelatin capsules such that each capsule contains 10 mg. of drug. The capsules are then administered to mammals in need of treatment for anxiety and/or depression or who are in pain or require sedation. Similarly an aqueous suspension can be prepared from a complex containing 5 parts of drug to 45 parts of polyethyleneglycol (molecular weight = 3000) to which one half-part by weight of a surfactant such as polyoxyethylene-sorbitan monooleate is added. Sufficient water is added to give a final concentration of 5 mg. of drug (as a polyoxyethylene complex) per ml. of suspension. The suspension is then administered by the oral route to a mammal requiring such medication.

The use of pharmaceutical formulations of drugs of formula I above as anti-anxiety and/or anti-depressant agents as anglgesics, as sedatives or as hypotensive agents is more explicitly set forth in the copending applications of Robert A. Archer, Ser. No. 413,009 and Ser. No. 413,010, filed this even day with parent application Ser. No. 413,012. According to those specifications, the dosage of drug represented by Formula I will vary from 0.001 to 100 mg. per day per patient or from 0.001 to 25 mg. per dose of a pharmaceutical formulation prepared as indicated above.

Prior art usages of PVP-drug combinations have without exception been directed toward providing materials of increased solubility for better oral absorption of the drug. Suprisingly, the PVP or polethylene glycol dispersions of the dibenzo[b,d] pyrans of Formula I above are not necessarily more soluble, but are able to maintain their solubility for long periods of time such as 90 days or longer. Apparently, the PVP or polyethylene glycol is able to stabilize a particular polymorphic form of the drug in which, ordinarily, in the absence of the dispersing agent, the soluble polymorphic form changes to a less soluble polymorphic form. For example, an aqueous suspension similar to that illustrated above can be prepared by taking 10 parts of a drug represented by formula I above, for example, 1-hydroxy-3-(1′,1′-dimethylheptyl)-6,6-dimethyl-6,6a,7,8,10,10a-hexahydro-9H-dibenzo [b,d]pyran-9-one, in finally divided amorphous state as obtained after evaporation of an acetone solution of the drug and mixing the amphorous drug with one part by weight of polyoxyethylene-sorbitan monooleate or other suitable surfactant. Sufficient water is added to this mixture so as to provide a dose level of 5 mg. of drug per ml. If the suspension is allowed to stand for a period of 4 days, the drug apparently changes its crystalline form and begins to change in aqueous suspension to a polymorphic form of drug which is little, if at all, absorbed upon oral administration and gives negligible blood levels. I have found that a PVP-dibenzo[b,d]pyran-9-one dispersion prepared as indicated above and as furnished by this invention does not "recrystallize" when held in suspension for periods up to 4 days but instead is maintained in its readily absorbable form. Thus, there is no decrease in oral absorption and drug effectiveness when using pharmaceutical formulations for oral administration prepared in accordance with this invention as compared with those prepared by conventional means.

I claim:

1. A dispersion of 2–20 parts of polyethyleneglycol having a molecular weight in the range 1000–6000, with one part of a compound of the formula

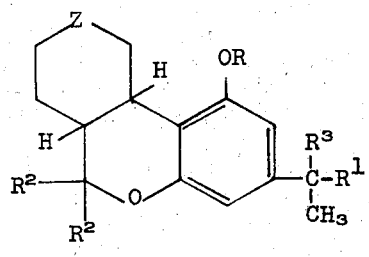

wherein Z is

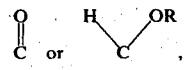

wherein each R is individually hydrogen or $C_1$-$C_3$ alkanoyl,
wherein $R^3$ is hydrogen or methyl,
wherein each $R^2$ is either hydrogen or methyl, and both $R^2$ groups are the same and wherein $R^1$ is $C_1$-$C_6$ alkyl [, or $C_2$-$C_6$ alkenyl].

2. A dispersion according to claim 1 wherein the compound is 1-hydroxy-3-(1′,1′-dimethylheptyl)-6,6-dimethyl-6,6a,7,8,10,10a-hexahydro-9H-dibenzo[b,d]-pyran-9-one.

* * * * *